United States Patent [19]

Boman

[11] Patent Number: 4,892,532
[45] Date of Patent: Jan. 9, 1990

[54] DISPOSABLE LIQUID-ABSORBING ARTICLE

[75] Inventor: Lars Boman, Mölndal, Sweden
[73] Assignee: Molnlycke AB, Gothenburg, Sweden
[21] Appl. No.: 150,406
[22] PCT Filed: May 20, 1987
[86] PCT No.: PCT/SE87/00250
 § 371 Date: Dec. 29, 1987
 § 102(e) Date: Dec. 29, 1987
[87] PCT Pub. No.: WO87/07117
 PCT Pub. Date: Dec. 3, 1987

[30] Foreign Application Priority Data

May 27, 1986 [SE] Sweden ................. 8602413

[51] Int. Cl.⁴ ........................................... A61F 13/16
[52] U.S. Cl. ...................................... 604/366; 604/378
[58] Field of Search ........................... 604/378–383, 604/365, 366, 358

[56] References Cited

U.S. PATENT DOCUMENTS

| | | | |
|---|---|---|---|
| 3,949,130 | 4/1976 | Sabee et al. | 604/378 |
| 3,955,577 | 5/1976 | Gellert et al. | 604/366 |
| 4,047,531 | 9/1977 | Karami. | |
| 4,075,382 | 2/1978 | Chapman et al. | 604/366 |
| 4,307,721 | 12/1981 | Tsuchiya et al. . | |
| 4,392,861 | 7/1983 | Butterworth et al. . | |
| 4,623,340 | 11/1986 | Luceri | 604/378 |
| 4,723,954 | 2/1988 | Pieniak | 604/378 |
| 4,753,834 | 6/1988 | Braun et al. | 604/378 |

FOREIGN PATENT DOCUMENTS

| | | | |
|---|---|---|---|
| 3525379 | 1/1987 | Fed. Rep. of Germany | 604/385.1 |
| 379635 | 10/1975 | Sweden . | |
| 2111836 | 7/1983 | United Kingdom | 604/366 |

*Primary Examiner*—Max Hindenburg
*Assistant Examiner*—K. M. Reichle
*Attorney, Agent, or Firm*—Young & Thompson

[57] ABSTRACT

Disposable liquid-absorbing article such as a diaper, a sanitary napkin or the like incorporating an absorption body (1) and a casing surrounding it. The distinguishing feature of the inventive article is that the body-contacting portion (5) of the casing is composed of a thin hydrophobic layer of fiber fabric of the spun-bonded type, and that there is applied between the casing portion and the absorption body (1) a likewise hydrophobic fiber fabric layer of the melt-bonded type.

6 Claims, 2 Drawing Sheets

DISPOSABLE LIQUID-ABSORBING ARTICLE

FIELD OF THE INVENTION

The present invention relates to a disposable liquid-absorbing article such as a diaper, a sanitary napkin or the like comprising an absorption body surrounded by a casing which is liquid permeable at least in its portion facing the user of the article.

BACKGROUND OF THE INVENTION

Disposable articles in the form of diapers, sanitary napkins and the like must meet very high demands with regard to the portion of the casing adapted for contact with the wearer's body during use of the article. On the one hand, this body-contacting portion must give a soft and pleasant feel to the skin for the wearer's comfort; that is the surface friction of the casing material should be low in order to avoid skin irritation caused by mechanical rubbing, and on the other hand the casing material in contact with the wearer's skin during use should be capable of remaining dry. Moreover, the portion in question should have an extremely high wear-resisting capacity to withstand wear from its contact with the wearer's skin. In addition, the surface layer must be capable of creating a certain distance between the skin and the absorption body in order to prevent rewetting the wearer's skin with fluid from the absorption body.

THE PRIOR ART

So far, there has been found no satisfactory method of fulfilling the requirements set forth above In general, the liquid-absorbing disposable articles of today have a hydrophobic fibrous layer placed in direct contact with the wearer's skin. Although this layer does in fact exhibit a certain protective effect against rewetting, it still lacks the capacity of presenting a well-functioning combination of surface softness and wear strength. To obtain a sufficient degree of wear strength in chemically bonded fiber fabrics, such large amounts of binding agent have had to be intermixed that the fibrous layer has become rough and given rise to an unpleasant feel when in touch with the skin.

It is also previously known to use melt-bonded types of fiber fabric consisting of thermoplastic fibers bonded to a surface pattern by means of melt bonding. As is the case with chemically bonded fiber fabrics, however, these latter layers as well become much too harsh with a high-density bonding pattern, whereas their wear strength will be insufficient when bonded too loosely.

Even the problem of creating the necessary spacing to the absorption body has remained unsolved with the types of prior art surface layers described in the foregoing.

In conventional articles there is frequently used a layer of cellulose wadding placed inside the hydrophobic surface layer, which per se provides a certain distance between surface layer and absorbent body, the cellulose wadding simultaneously serving to somewhat stabilize the absorption body which is generally composed of pulp fibers. There is however the drawback associated with cellulose wadding that it has a both liquid absorbing and liquid distributing effect, permitting in this manner liquid to spread and remain collected immediately underneath the surface layer of these known articles. Therefore, such a solution is far from satisfactory with regard to rewetting.

Previous attempts have also been made in an effort to overcome the problem of rewetting by placing an insulation layer of airlaid hydrophobic fibers between the outer casing and the absorption body. This has indeed considerably eliminated rewetting while having instead created other significant drawbacks since it is hardly useful from a manufacturing viewpoint because of the difficulties associated with the application of such layers at high manufacturing speeds while simultaneously maintaining a highquality performance.

A most vital aspect, which has so far been neglected by manufacturers of diapers and sanitary napkins in the production of suitable casing portions intended for direct contact with the wearer's body, is the instantaneous absorption. If a casing layer is produced which is thick enough to prevent rewetting, the instantaneous absorption will be too low due to the tendency of overdimensioned hydrophobic layers to produce a liquid-repellent effect, which many times gives rise to leakage in conventional diapers and sanitary napkins.

Beyond the demands on wear strength, low surface friction and softness, there are thus also placed contradictory demands on the liquid insulating capacity of the liquid permeable casing.

BRIEF SUMMARY OF THE INVENTION

With the present invention, however, there has been obtained a casing and an insulating layer intended for direct contact with the wearer's skin, said layer being superior to previously known material layers designed for this purpose. This object has been fulfilled in that the liquid permeable body-contacting casing portion of an article made in accordance with the invention consists of a thin, spun-bonded fibrous fabric layer composed of a hydrophobic material, and in that there is applied between said casing portion and the absorption body a similarly constructed, hydrophobic fibrous layer of melt-bonded fiber fabric, the surface weight of this last-mentioned layer being greater than that of the aforementioned casing portion.

BRIEF DESCRIPTION OF THE DRAWINGS

The invention will be described in more detail below with reference to two exemplary embodiments illustrated in the accompanying drawings, of which FIGS. 1 and 2 show a first embodiment of an absorbent article made according to the invention, whereas

DETAILED DESCRIPTION OF THE INVENTION

In the two embodiments shown, the absorption body 1 consists of so-called cellulose fluff pulp. On the side of the article facing the wearer during use, there is applied over the absorption body a hydrophobic fiber fabric layer 2 of the so-called melt-bonded type. This fabric layer consists of heatbondable fibers made of polypropylene, for example, which are only locally heat-bonded for creating a voluminous insulating layer having fibrous, cushionlike protuberances formed between the local connecting points. The insulating fiber cushions serve to prevent rewetting with fluid from the absorption body, imparting to the layer in addition a spring back effect which is essential in this context because of the significant compression stresses the article is subjected to during use. The fiber fabric layer 2 obtained in this manner will have a high surface friction thereby making it useful as a reinforcing means for the absorption body 1, which has in itself a weak integrity and a lump-forming tendency due to the stresses occurring during use. Advantageously, the fiber fabric layer 2 can have edge portions 3, 4 extending over the side margins of the absorption body 1, said edge portions 3, 4 preventing the side margins from rewetting the wearer's skin. For the sake of providing an effective insulation while simultaneously permitting maximum through-flow of liquid to the absorption body 1, the fiber fabric layer 2 should have a surface weight in the order of 20–30 g/m².

Figure 1:
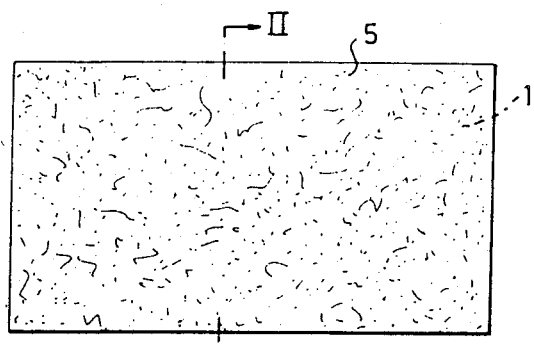
Figure 2:
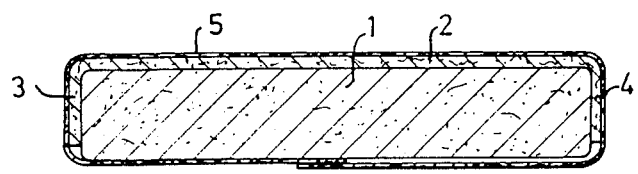

In the embodiment of FIGS. 1 and 2, the absorption body 1 as well as the fiber fabric layer 2 are enclosed in a casing 5 made of a hydrophobic fibrous fabric of the so-called spun-bonded type. This fiber fabric is produced of endless fibers of polypropylene for example, giving a smooth, soft surface with a low surface friction and imparting simultaneously to said layer a very high strength. The fiber fabric layer 5 of the spun-bonded type should be made very thin and have a weight of less than 15 g/m².

Such a thin layer of fiber fabric is necessitated by the need of securing a sufficiently high instantaneous through-flow of liquid from the user to the absorption body 1.

In the first exemplary embodiment shown in FIGS. 1 and 2, the fiber fabric layer 2 of the melt-bonded type is not connected to the casing itself, which is an advantage in that the two layers are then somewhat mutually displaceable, reducing thereby the irritating frictional contact with the skin of the user.

Figure 3:
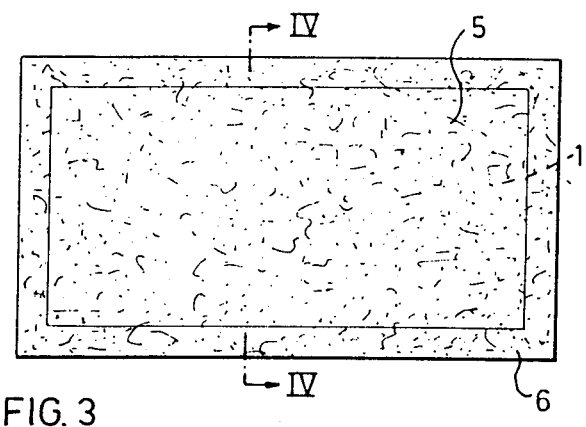
FIGS. 3 and 4 show a second embodiment thereof.
Figure 4:
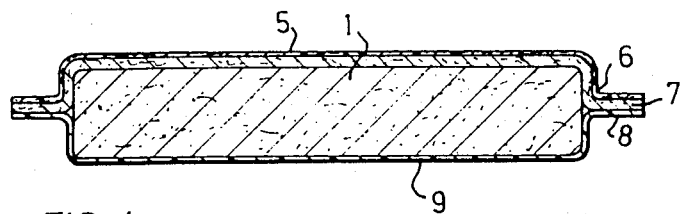

In the second embodiment shown in FIGS. 3 and 4, the portions corresponding to similar portions in the first embodiment shown in FIGS. 1 and 2 have been given the same reference numerals.

In both of the two embodiments shown, the two fiber fabric layers 2, 5 cover the body-contacting side of the absorption body during use and, as indicated by the second embodiment shown in FIGS. 3 and 4, extend further with edge portions 6,7 beyond the margins of the absorption body where they are affixed by melt-bonding both to one another and to the edge portions 8 of a liquid-tight plastic film 9 applied to the opposite side of the absorption body. By securing the edge portions with the casing 5, 9, the wear strength of the article made in accordance with the second embodiment shown here will be increased. Owing to the high surface friction in the melt-bonded type of fiber fabric layer 2, there has further been accomplished a good frictional bonding with the absorption body 1 which, as a result of the frictional affixation imparted to its casing 5, 9 by the layer 2, will then be anchored thereto, which also adds to its strength.

As is also the case with the first embodiment shown in FIGS. 1 and 2, the two fiber fabric layers of the second embodiment shown in FIGS. 3 and 4 are not interconnected within the area of the article facing the wearer during use.

The invention is not restricted to the embodiments described and illustrated in the foregoing, since a plurality of modifications are conceivable within the scope of the patent claims.

I claim:

1. A disposable liquid-absorbing article such as a diaper, a sanitary napkin or the like comprising an absorption body (1), a casing (5) surrounding said body (1) and having a portion adapted to face the user of the article, said casing (5) being liquid permeable at least in its portion adapted to face the user of the article, characterized in that the liquid-permeable portion of the casing (5) consists of a thin, spun-bonded fibrous fabric layer composed of a hydrophobic material, and in that a similarly constructed hydrophobic fibrous layer of melt-bonded fiber fabric is applied between said casing portion and the absorption body, the latter said layer (2) having a weight per unit area which is greater than that of said casing portion.

2. An absorbent article according to claim 1, characterized in that said casing portion made of spun-bonded fiber fabric has a weight less than approx. 15 g/m².

3. An absorbent article according to claim 2, characterized in that the layer (2) made of melt-bonded fiber fabric has a weight in the order of 20–30 g/m².

4. An absorbent article according to claim 1, characterized in that the casing in its entirety consists of a thin spun-bonded fiber fabric layer.

5. An absorbent article according to claim 1, characterized in that the liquid permeable casing portion adapted to face the user of the article extends beyond and is connected around the absorption body (1) with edge portions (8) of a liquid impermeable, second casing portion (9) applied to the side of the absorption body which is opposite the first-mentioned casing portion, and in that also the melt-bonded fiber fabric layer (2) placed inside the liquid permeable casing portion extends beyond the absorption body while being secured between edge portions (6, 8) of said first-mentioned and said second casing portions.

6. An absorbent article according to claim 1, characterized in that the two fiber fabric layers (2,5) of the spun-bonded and the melt-bonded type, respectively, are non-secured in relation to one another within the liquid permeable portion during use of the article.

* * * * *